(12) United States Patent
Pak et al.

(10) Patent No.: US 6,635,426 B2
(45) Date of Patent: Oct. 21, 2003

(54) MIXED INTERCALATOR AND ELECTROCHEMICAL DETECTION OF DNA USING SAME

(75) Inventors: Youngmi Kim Pak, Kunpo-si (KR); James Jungho Pak, Kunpo-si (KR); Sanghee Kim, Seoul (KR); Hong-Kyu Lee, Seoul (KR)

(73) Assignee: Mitocon Ltd., Seoul (KR)

( * ) Notice: Subject to any disclaimer, the term of this patent is extended or adjusted under 35 U.S.C. 154(b) by 7 days.

(21) Appl. No.: 09/927,669

(22) Filed: Aug. 10, 2001

(65) Prior Publication Data

US 2003/0039975 A1 Feb. 27, 2003

(30) Foreign Application Priority Data

Feb. 6, 2001 (KR) .......................................... 2001-5667

(51) Int. Cl.[7] ............................ C12Q 1/68; C12P 19/34; C12M 1/34; C07H 21/02; C07H 21/04

(52) U.S. Cl. .................................. 435/6; 435/6; 435/7.1; 435/91.1; 435/91.2; 435/287.2; 536/22.1; 536/23.1; 536/24.3; 536/24.31; 536/24.32; 536/24.33; 436/94; 546/1

(58) Field of Search ............................ 435/6, 7.1, 91.1, 435/91.2, 287.2; 536/22.1, 23.1, 24.3–24.33; 546/1; 436/94

(56) References Cited

U.S. PATENT DOCUMENTS 6,368,807 B2 * 4/2002 Makino et al. ................. 435/6

* cited by examiner

*Primary Examiner*—Jeffrey Siew
(74) *Attorney, Agent, or Firm*—Anderson Kill & Olick, PC

(57) ABSTRACT

Described in the present invention are a highly sensitive method for electrochemically detecting a DNA using a novel mixed intercalator and a detection kit useful for practicing said method.

4 Claims, 2 Drawing Sheets

MIXED INTERCALATOR AND ELECTROCHEMICAL DETECTION OF DNA USING SAME

FIELD OF THE INVENTION

The present invention relates to a highly sensitive method for electrochemically detecting a DNA using a unique combination of compounds as a mixed intercalator and a detection kit using same.

BACKGROUND OF THE INVENTION

DNA chips have been widely used in gene and molecular biology researches such as the measurement of RNA expression in a large scale, detection of mutant genome DNAs, gene diagnosis, pharmacogenomics and medicine, as they can detect RNAs or DNAs contained in a sample much more efficiently than the conventional Southern blot or Northern blot method.

Generally, DNA chips detect a target DNA, for example, by way of accumulating hundreds of thousands of probe DNA fragments, each having a specified base sequence, on a very small chip surface, contacting the probe DNA fragments with a single strand of the target DNA labeled with a fluorescent material to induce hybridization, and identifying the hybridized DNA by laser irradiation.

However, the above method has the disadvantages that it requires the use of an expensive optical apparatus including a laser scanner and the cost of fluorescent labeling is high. Further, it is difficult to quantitatively determine the amount of the target DNA in a sample from the luminescent intensity.

Accordingly, there have been numerous efforts to solve the above-mentioned problems. For instance, Clinical Microsensors Inc. suggests a method of detecting a DNA by binding a redox-active material, e.g., a transition metal complex, on a selected site of a single-stranded probe DNA, bringing a single-stranded target DNA into contact with the resulting probe DNA to induce hybridization, and measuring the change in the electron transporting rate attributable to the hybridization. In addition, Japanese Patent Publication No. 2000-125865 provides a method of detecting a gene of a specimen DNA by allowing a single-stranded sample DNA to interact with a single strand probe DNA immobilized on an electrode surface in the presence of an electrochemically active intercalator to form a hybridized DNA carrying the intercalator, followed by determining the current which flows through the intercalator.

These methods, however, still exhibit a limited sensitivity for quantitative DNA detection, and thus, there has existed a need to develop a DNA detection method having a higher sensitivity.

SUMMARY OF THE INVENTION

Accordingly, it is an object of the present invention to provide an improved method for detecting a DNA with a high sensitivity.

It is another object of the present invention to provide a novel intercalator and a detection kit which are suitable for practicing the method.

In accordance with one aspect of the present invention, there is provided a method for detecting a DNA having a specified base sequence (target DNA), which comprises bringing a single strand of the target DNA (target ssDNA) into contact with a single strand probe DNA (probe ssDNA) bonded on the surface of an electrode equipped with an output terminal to form a double strand DNA (dsDNA), adding a mixed intercalator consisting of compounds of formulae (I) and (II) to intercalate the dsDNA therewith, and determining the current generated when a voltage is applied to the electrode.

In accordance with another aspect of the present invention, there is provided an alternative method for detecting a DNA having a specified base sequence (target DNA), which comprises bringing a single strand of the target DNA (target ssDNA) into contact with a single strand probe DNA (probe ssDNA) bonded on the surface of an electrode equipped with an output terminal in the presence of a mixed intercalator consisting of compounds of formulae (I) and (II) to obtain a double strand DNA intercalated by said compounds, and determining the current generated when a voltage is applied to the electrode:

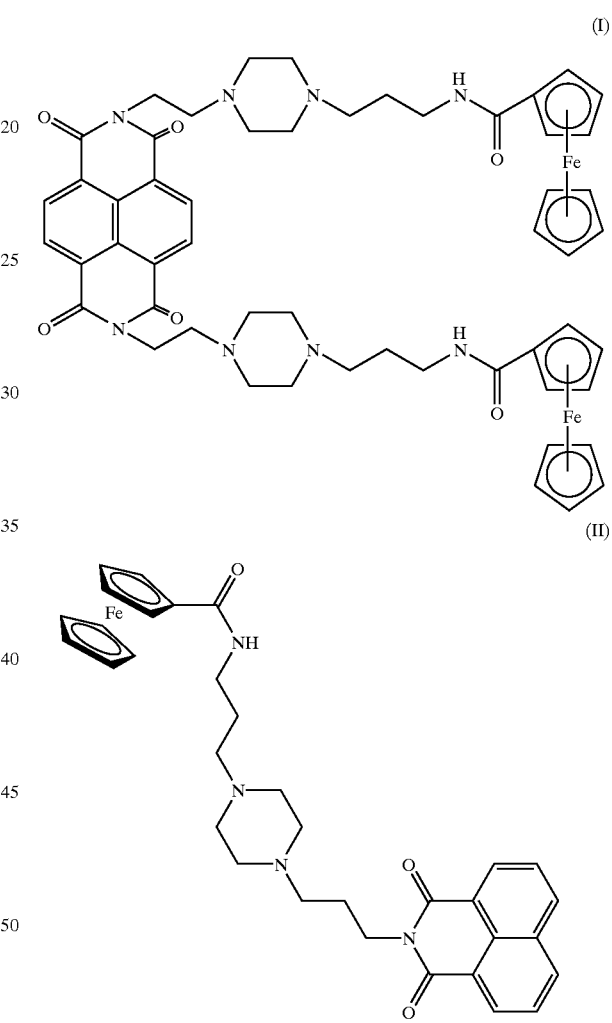

In accordance with still another aspect of the present invention, there is provided a DNA detection kit used in practicing the method, comprising a DNA sensor having a layer of single strand probe DNAs bonded on the surface of an electrode equipped with an output terminal and a mixed intercalator consisting of compounds of formulae (I) and (II); and the mixed intercalator.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
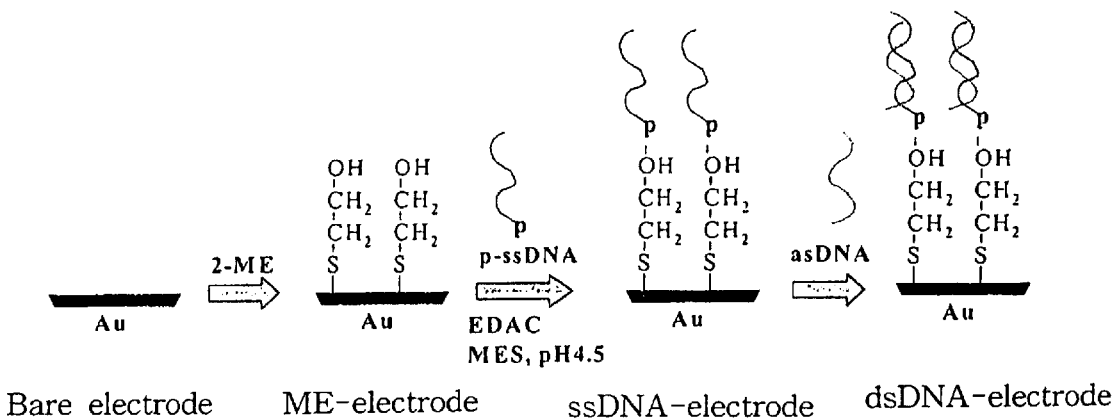
FIG. 1: a schematic procedure for the preparation of a dsDNA-electrode in accordance with one embodiment of the present invention.

The probe ssDNA used in the present invention may be obtained from a DNA isolated from a biological sample or chemically synthesized.

A probe ssDNA-electrode which comprises an electrode having an output terminal and a probe ssDNA bonded to one surface thereof is prepared, e.g., by reacting the bare electrode surface with a compound having a terminal —SH group and a functional group such as —OH, —COOH and —NH$_3$ at the other end, e.g., 2-mercaptoethanol, 3-mercaptobutanol and 3-mercaptopropionic acid, to obtain a coated electrode which has a monolayer of the compound bonded to the electrode through sulfide bonds, and then, reacting an ssDNA having a phosphoric acid group at its 5'-end with the coated electrode, wherein the phosphoric acid group bonds with the functional group such as —OH, —COOH and —NH$_3$ exposed on the coated electrode. This reaction may be performed in a buffer solution of pH 4.5 to 6.4 in the presence of an acid catalyst such as 2-(N-morpholino)ethanesulfonic acid (MES) and the resulting electrode is designated "ssDNA-electrode". Alternatively, an ssDNA having a —SH group instead of a phosphoric acid group at its 5'-end may be immobilized directly to the surface of a bare electrode, followed by filling the open surface of the resulting electrode with, e.g., 2-mercaptoethanol.

The ssDNA-electrode thus prepared is treated with a solution containing a single strand target DNA at room temperature for a period ranging from 12 to 48 hours, preferably 24 hours, inducing hybridization between the probe DNA and the target DNA to form a dsDNA and the electrode having such a dsDNA is designated "dsDNA-electrode".

During or after the process of forming the dsDNA, a mixed intercalator of the present invention, consisting of N,N-bis[[4-(3-ferrocenecarboxamidopropyl)piperazinyl]propyl]naphthalene-1,4,5,8-tetracarboxylic acid of formula (I), designated IC1, and N-[[4-(3-ferrocenecarboxamidopropyl)piperazinyl]propyl]-1,8-naphthalene imide of formula (II), designated IC2, is allowed to be intercalated and incorporated in the formed dsDNA. The inventive mixed intercalator is capable of forming a stable intercalation complex with the dsDNA, while it does not form stable adducts with ssDNAs.

Consequently, in case the DNA present in a sample is capable of hybridizing with the probe DNA, the inventive mixed intercalator which contains the ferrocene moieties of IC1 and IC2 having desirable redox properties work together to facilitate the electron transfer process when a potential is applied to the dsDNA-electrode.

It is understood that IC1 intercalates selectively into a site which is separated by 3 to 5 pairs of bases from the next site, while the insertion of one molecule of IC2 requires only one pair of base. But, the use of IC2 alone does not provide an intercalated dsDNA having desirable properties. When a combination of IC1 and IC2 is used in a weight ratio of 1:0.1~10, preferably 1:0.5~5, IC2 is inserted into sites which are not occupied by IC1 and they work together to create a synergistic effect of enhancing the electron transport process through the dsDNA chain. IC2 further acts as a supersensitizer for the reduction of oxidized IC1.

Based on the method of the present invention, it is possible to identify a target DNA in a sample by way of using a DNA detection kit comprising a DNA sensor and the inventive mixed intercalator, the sensor containing a single strand probe DNA which is hybridizable with the target DNA and immobilized on an electrode equipped with an output terminal. Such a sensor may contain a plurality of electrodes coated with various probe ssDNAs for detecting a multiple number of DNAs in a sample. As the current density obtained as a result of the present invention depends on the concentration of the target ssDNA in the sample, it is possible to quantify the amount thereof.

The current density may be measured by any method, e.g., cyclic voltametry, differential pulse voltametry and potentiostat.

As described above, the method of the present invention provides a simple and sensitive means for assessing the identity and the amount of a target DNA in a sample.

The following Examples are given for the purpose of illustration only, and are not intended to limit the scope of the invention.

EXAMPLE 1

Preparation of a Probe ssDNA-electrode (Step 1) Coating of Au Electrode

An Au electrode with an area of 2 mm$^2$ (MF-2014 AUE gold electrode, BAS, IN, USA) was sequentially washed with hot 2 M NaOH for 5 min., and then, with concentrated nitric acid for 5 min., followed by two cycles of ultrasonic-treatment in distilled water, each for 3 min. The electrode was dipped in an aqueous 0.1 M sulfuric acid solution, and the voltage applied thereto was cycled between 0 to 1.5 V at a rate of 100 mV/s using a voltammetric analyzer (BAS, CV-50W, IN, USA), until the current originating from contaminants was no longer detectable, to determine a basal line. The bare electrode thus obtained was treated with a 1 mM 2-mercaptoethanol (2-ME) solution for 2 hr to induce sulfide bond formation between the —SH group of 2-mercaptoethanol and the electrode surface. The resulting electrode was coated with a monolayer of covalently bonded —S—CH$_2$CH$_2$—OH, the terminal —OH group being extended outwards.

(Step 2) Preparation of ssDNA-electrode

Using an oligonucleotide synthesizer, sense and anti-sense oligonucleotides of sequence numbers: 1 and 2 were prepared, and then, a phosphoric acid group was joined to the 5'-end of the sense oligonucleotide. 1-ethyl-3-(3-dimethylaminopropyl)carbodiimide hydro-chloride (EDAC) and the sense oligonucleotide (ssDNA) were dissolved to concentrations of 1 µg/µl and 1 mM, respectively, in a 40 mM 2-(N-morpholino)ethanesulfonic acid (MES) buffer solution (pH 4.5), and the coated electrode prepared in (Step 1) was treated with the solution for 24 hrs to obtain a ssDNA-electrode having the phosphoric acid groups of the ssDNA bonded with the —OH groups of the electrode surface.

EXAMPLE 2

Detection of DNA (Step 1) Formation of Hybrid DNA

1 µl of anti-sense DNA (asDNA) (1 nmol/µl) of sequence number: 2 was added to 30 µl of a hybridizing solution (0.09 µg/µl of salmon spermatozoon DNA, 0.5 µg/µl of acetylated cow serum albumin, 27 mM MES (free acid), 74 mM MES (sodium salt), 0.89 M NaCl, 0.01% Tween 20 and 20 mM EDTA), and the ssDNA-electrode prepared in Example 1 was reacted with the solution at 37° C. for 24 hrs. to form a hybrid DNA. The resulting electrode was washed with a washing solution (27 mM MES (free acid), 74 mM MES (sodium salt), 26 mM NaCl and 0.01% Tween 20) at 37° C. for 15 min. and the washing procedure was repeated three-times to obtain a dsDNA-electrode which has double-stranded DNAs attached to the electrode. The preparative procedure of such a dsDNA-electrode is schematically showed in FIG. 1.

(Step 2) Combination of dsDNA and Intercalator

N,N-bis[[4-(3-ferrocenecarboxamidopropyl)piperazinyl]propyl]-naphthalene-1,4,5,8-tetracarboxylic acid of formula (I) (IC1) and N-[[4-(3-ferrocenecarboxamidopropyl)piperazinyl]propyl]-1,8-naphthalene imide of formula (II) (IC2) were dissolved in distilled water, each to the concentration of 40 μM, and the dsDNA-electrode prepared in (Step 1) was treated with the solution at room temperature for 10 min. to obtain a dsDNA-electrode wherein both IC1 and IC2 were incorporated in the dsDNA as intercalators. For comparison, another dsDNA-electrode intercalated only by IC1 was prepared by a similar method.

Figure 2:
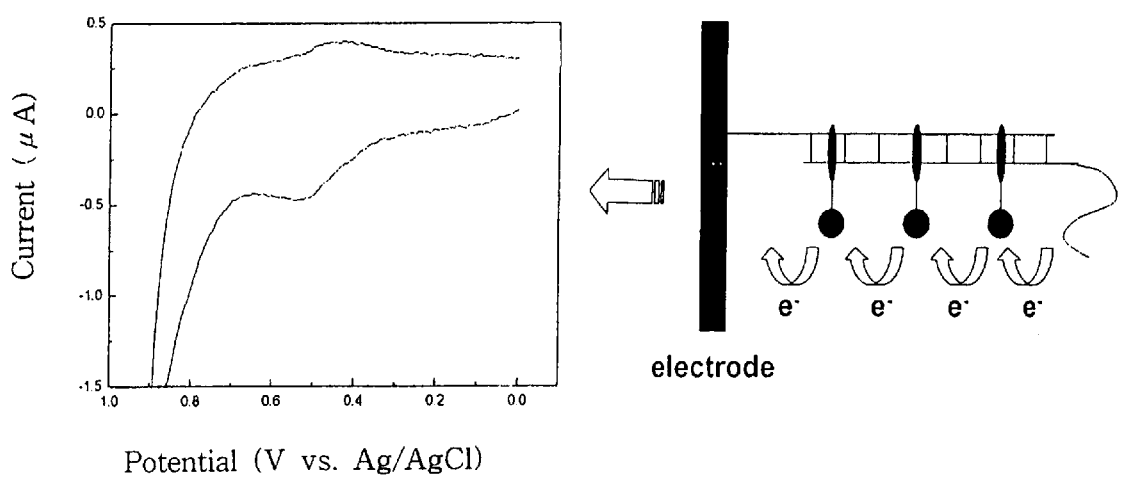
FIG. 2: a schematic representation of the electron transfer through a layer of an intercalator and the typical cyclic current—voltage curve obtained therefor.

A voltage was applied to a tri-electrode system which comprises one of the prepared dsDNA-electrodes as a working electrode, Ag/AgCl as a reference electrode and Pt wire as a counter electrode, and the current generated by the applied voltage-induced redox reactions in the electrolyte solution (0.1 M KCl) was measured with a voltammetric analyzer (BAS, CV-50W, UK). In this case, the current is transferred to the electrode via IC1 and IC2, or via IC1 alone, and the amount of the current was obtained from the cyclic voltammetry (see FIG. 2).

Figure 3:
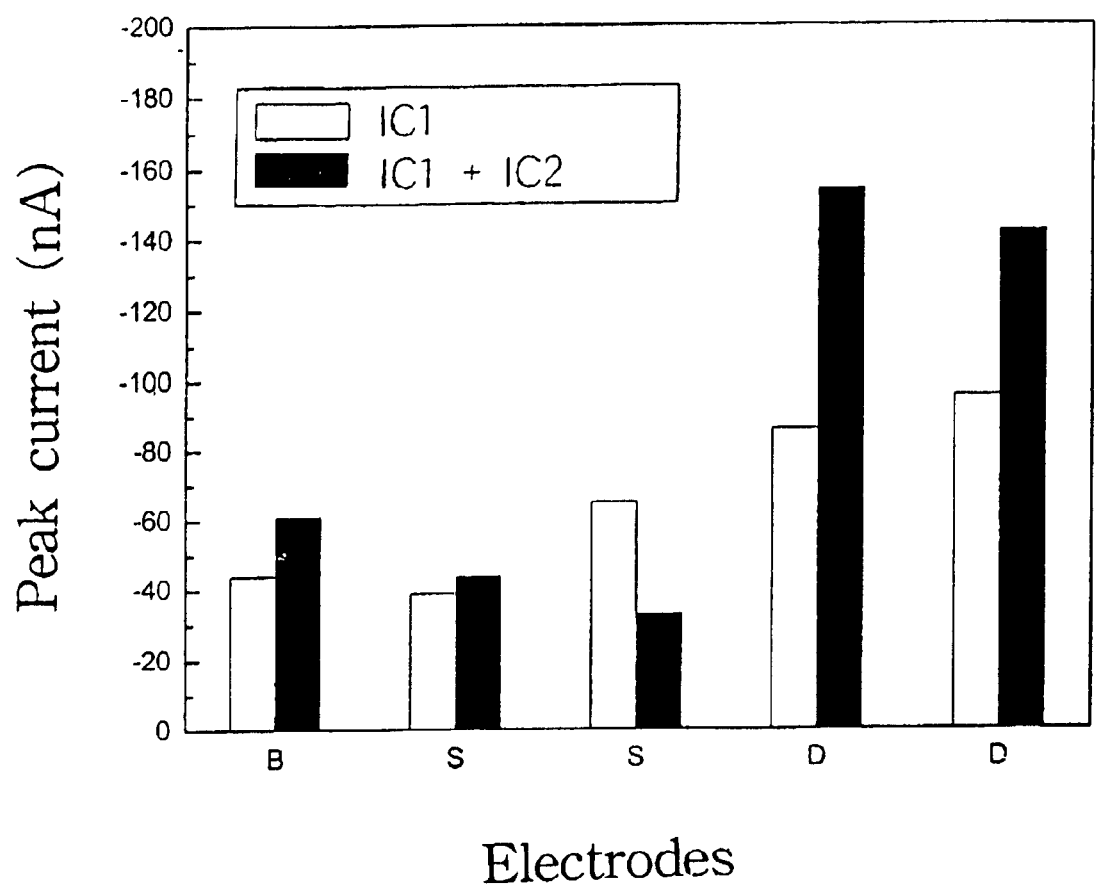
FIG. 3: peak current values obtained with a conventional single intercalator and the inventive mixed intercalator.

As shown in FIG. 3, the peak current obtained for the system containing the conventional intercalator, i.e., IC1 alone, was not nearly as high as the currents obtained for two cases of the inventive mixed intercalator (IC1 and IC2). In this figure, B refers to the basal line mentioned in (Step 1) of Example 1; S, an ssDNA-electrode; and D, a dsDNA-electrode (two independent cases). The markedly high current density obtained for the inventive dsDNA-electrode may be attributed to the ability of IC2 to occupy sites that are inaccessible by IC1.

As described above, in accordance with the method of the present invention, an unknown DNA can be assayed quantitatively with a high sensitivity.

While the embodiments of the subject invention have been described and illustrated, it is obvious that various changes and modifications can be made therein without departing from the spirit of the present invention which should be limited only by the scope of the appended claims.

What is claimed is:

1. A method for detecting a DNA having a specified base sequence (target DNA), which comprises bringing a single strand of the target DNA (target ssDNA) into contact with a single strand probe DNA (probe ssDNA) bonded on the surface of an electrode equipped with an output terminal to form a double strand DNA (dsDNA), adding a mixed intercalator consisting of compounds of formulae (I) and (II) to intercalate the dsDNA therewith, and determining the current generated when a voltage is applied to the electrode:

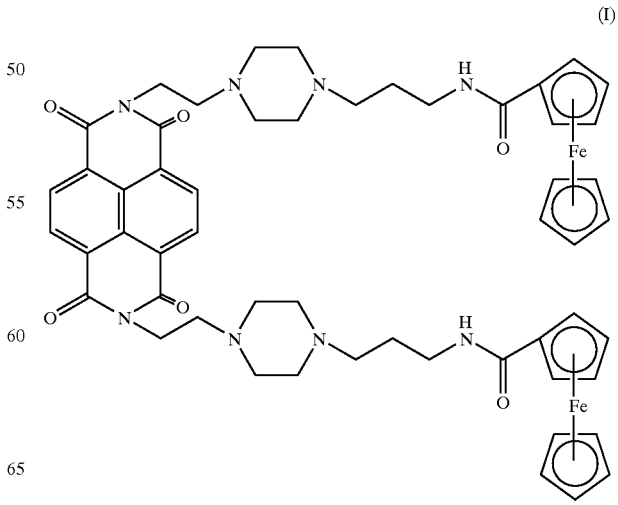

(II)

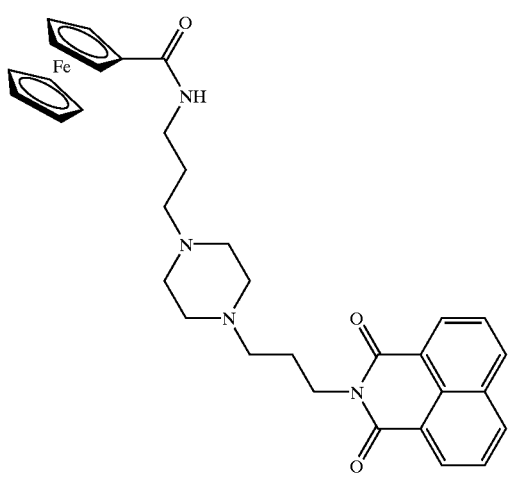

2. A DNA detection kit used in practicing the method of claim 1, comprising a DNA sensor having a layer of single strand probe DNAs bonded on the surface of an electrode equipped with an output terminal and a mixed intercalator consisting of compounds of formulae (I) and (II).

3. A mixed intercalator which consist s of compounds of formulae (I) and (II).

4. A DNA detection kit used in practicing the method of claim 1, comprising a DNA sensor having a layer of single strand probe DNAs bonded on the surface of an electrode equipped with an output terminal and a mixed intercalator consisting of compounds of formulae (I) and (II).

* * * * *

```
                        SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<221> NAME/KEY: misc_feature
<223> OTHER INFORMATION: synthetic sense oligonucleotide

<400> SEQUENCE: 1
cctaaccaga tttcaaattt tatcttttt                                    28

<210> SEQ ID NO 2
<211> LENGTH: 28
<212> TYPE: DNA
<213> ORGANISM: Artificial Sequence
<220> FEATURE:
<221> NAME/KEY: misc_feature
<223> OTHER INFORMATION: antisense of SEQ ID NO: 1

<400> SEQUENCE: 2
aaaagataaa atttgaaatc tggttagg                                     28
```